(12) United States Patent
McCartney

(10) Patent No.: US 6,730,220 B2
(45) Date of Patent: May 4, 2004

(54) KIDNEY DIALYSIS MACHINE

(76) Inventor: John McCartney, 669 Wyndamere Rd., Lewisberry, PA (US) 17339

( * ) Notice: Subject to any disclaimer, the term of this patent is extended or adjusted under 35 U.S.C. 154(b) by 152 days.

(21) Appl. No.: 10/099,411

(22) Filed: Mar. 16, 2002

(65) Prior Publication Data

US 2002/0130073 A1 Sep. 19, 2002

Related U.S. Application Data

(60) Provisional application No. 60/276,462, filed on Mar. 16, 2001.

(51) Int. Cl.$^7$ ................................................ B01D 61/30
(52) U.S. Cl. .................... 210/241; 210/321.6; 210/541; 210/646; 604/5.01; 604/6.09; 138/108; 138/110; 248/129
(58) Field of Search .............................. 210/241, 321.6, 210/321.71, 646, 541; 604/4.01, 5.01, 6.01, 6.09; 138/106, 108, 110; 248/129

(56) References Cited

U.S. PATENT DOCUMENTS

| | | | | | |
|---|---|---|---|---|---|
| 5,744,027 A | * | 4/1998 | Connell et al. | ............ | 210/96.2 |
| 5,895,571 A | * | 4/1999 | Utterberg | ..................... | 210/241 |
| 5,948,251 A | * | 9/1999 | Brugger | ..................... | 210/252 |
| 6,143,181 A | * | 11/2000 | Falkvall et al. | ............. | 210/646 |
| 6,197,197 B1 | * | 3/2001 | Peterson et al. | ............ | 210/646 |

* cited by examiner

*Primary Examiner*—Joseph W. Drodge
(74) *Attorney, Agent, or Firm*—Hooker & Habib, P.C.

(57) ABSTRACT

A kidney dialysis machine includes a number of flexible members extending from the machine to corresponding receptacles at a patient station. The flexible members are arranged in a cable bundle at a point intermediate of the machine and the ends of the members. A retaining member is wrapped around the bundle to hold the bundle together. The retaining member is attached to a spring that has one end connected to the retaining member and an opposite end attached to the kidney dialysis machine. The spring holds the bundle off the floor.

8 Claims, 2 Drawing Sheets

FIG. 1 – PRIOR ART

KIDNEY DIALYSIS MACHINE

This application claims the benefit of U.S. Provisional Application No. 60/276,462, filed Mar. 16, 2001.

FIELD OF THE INVENTION

This invention relates to kidney dialysis machines.

BACKGROUND OF THE INVENTION

A patient with kidney disease requires haemodialysis to remove waste products and water from the patient's blood. The blood is flowed from the patient through semi-permeable membranes in a kidney dialysis machine, also known as an artificial kidney. The treated blood flows back to the patient. A dialysis session may take about four hours and a patient may require dialysis three times a week.

A dialysis patient is treated at a patient station where the kidney dialysis machine is located. A conventional kidney dialysis machine includes a wheeled housing that enables the machine to be moved among a number of different patient stations. Extending from the housing are a number of flexible members including tubes, power cables, data cables and the like that are connected to peripheral receptacles, outlets or plugs at the patient station.

During patient treatment the free ends of some of the tubes are connected to one or more receptacles at the patient station. The receptacle connections must be sterile. If a tube were inadvertently pulled from a receptacle and touched the floor, the tube and receptacle connection must be sterilized before the tube is reconnected to the receptacle.

The flexible members have a sufficient length to enable the machine to be spaced a convenient distance from the receptacle, electrical outlets, and other connections. This enables some freedom in positioning the kidney machine within a work area adjacent the connections of the patient station, or readjusting the position of the machine within such area.

However, portions of the flexible members may end up on the floor of the patient station. A tangled mass of tubes, cables and wires can form on the floor next to the machine. A tangled member may be knotted with a portion of itself or another member. When moving the kidney machine the flexible members can be caught on or tangled with the machine itself, or can be caught in or run over by the machine wheels. Caught or knotted members could be pulled and disconnected from the receptacle or other connection points when the machine is moved about the patient station. Resterilization of the pulled members may be required, or the pulled members or their connections may be damaged. The wheels may roll over the flexible members and damage them.

Thus there is a need for an improved kidney dialysis machine. The flexible members should have a length sufficient to enable the machine to be conveniently positioned within the work area but should not tangle or catch on the machine if the machine is moved within the work area.

SUMMARY OF THE INVENTION

The invention is an improvement to a conventional dialysis machine that resists catching or tangling of the flexible members when the machine is moved within a work area.

The flexible members are arranged in a bundle at a point intermediate of the machine and the ends of the members. A retaining member is wrapped at least partially around the bundle to hold the bundle together. The retaining member is attached to a spring that has one end connected to the retaining member and an opposite end attached to the kidney dialysis machine. The spring holds the retaining member above the floor such that the bundle is held off the floor and cannot be caught in the wheels of the machine. Preferably the spring is attached to the machine near the top of the machine so that the spring is held above the floor as much as possible.

If desired, additional retaining members can extend along the length of the flexible members on either side of the said retaining member. Preferably the additional retaining members are spaced sufficiently close together to effectively form a cable of flexible members extending from the machine and beyond the retaining member attached to the holding spring. The individual members separate from the cable to extend to respective connections at the ends of the individual members. The retaining members maintain the axial alignment of the flexible members along the cable and resist knots from forming in the flexible members.

The retaining members can be conventional cable ties. The ties are inexpensive and readily available in a number of different sizes and configurations. The holding spring is preferably a metal coil tension spring that has one end attached to a cable tie and the other end attached to the machine. Preferably the tension spring has looped or coiled ends that form convenient attachment points. The spring may be attached to a preexisting connection member on a conventional dialysis machine.

In yet other possible embodiments of the present invention the retaining members may be one or more tubular sleeves.

In yet other possible embodiments of the present invention the machine can have a mounting structure specifically designed to mount the holding spring of the present invention. In yet other embodiments of the present invention the spring and one or more retaining members can be supplied as a conversion kit for existing machines. The kit may also include mounting hardware, such as threaded fasteners or magnets, to mount the end of the spring to the machine.

Other objects and features of the invention will become apparent as the description proceeds, especially when taken in conjunction with the accompanying drawings illustrating the invention, of which there are two sheets of one embodiment.

DESCRIPTION OF THE PREFERRED EMBODIMENT

Figure 1:
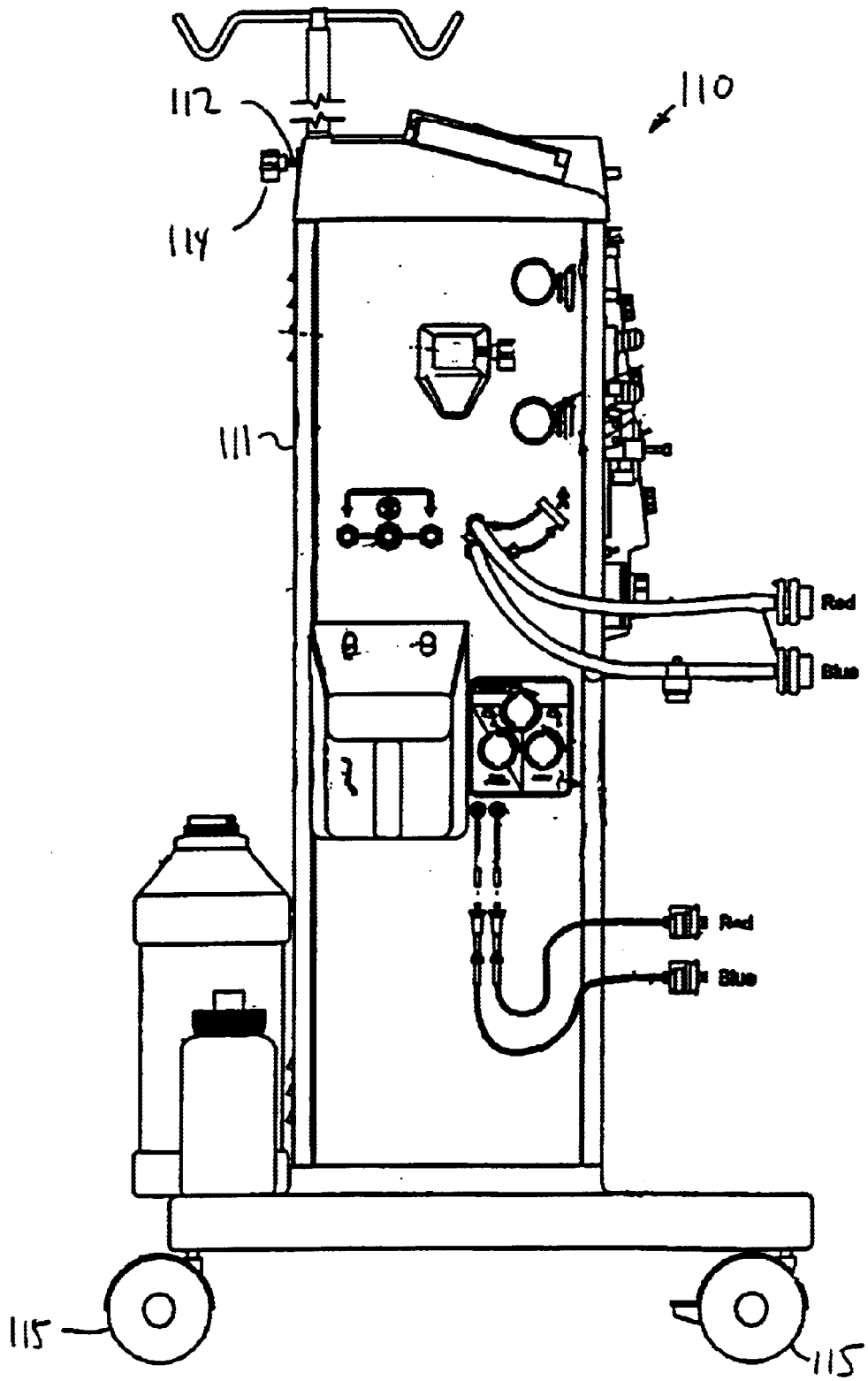
FIG. 1 is a simplified view of the left side of a conventional kidney dialysis machine.

FIG. 1 is a simplified view of the left side of a conventional kidney dialysis machine 110. The machine 110 may be a Baxter Model 1550 manufactured by Baxter International Inc., Deerfield, Ill. or functional equivalent. The machine 110 may also be of the kind disclosed in Connell et al. U.S. Pat. No. 5,744,027 incorporated by reference herein or the references cited therein, each of which references are also incorporated by reference herein.

The machine 110 has a machine housing 111 that contains membrane apparatus (not shown) for performing dialysis. The illustrated machine 110 includes a threaded shaft 112 extending from the back of the housing 111. The shaft 112 is located near the top of the housing and a knob 114 is threaded on the shaft 112. The housing is mounted on wheels 115 that support the housing on the floor of a patient station.

Figure 2:
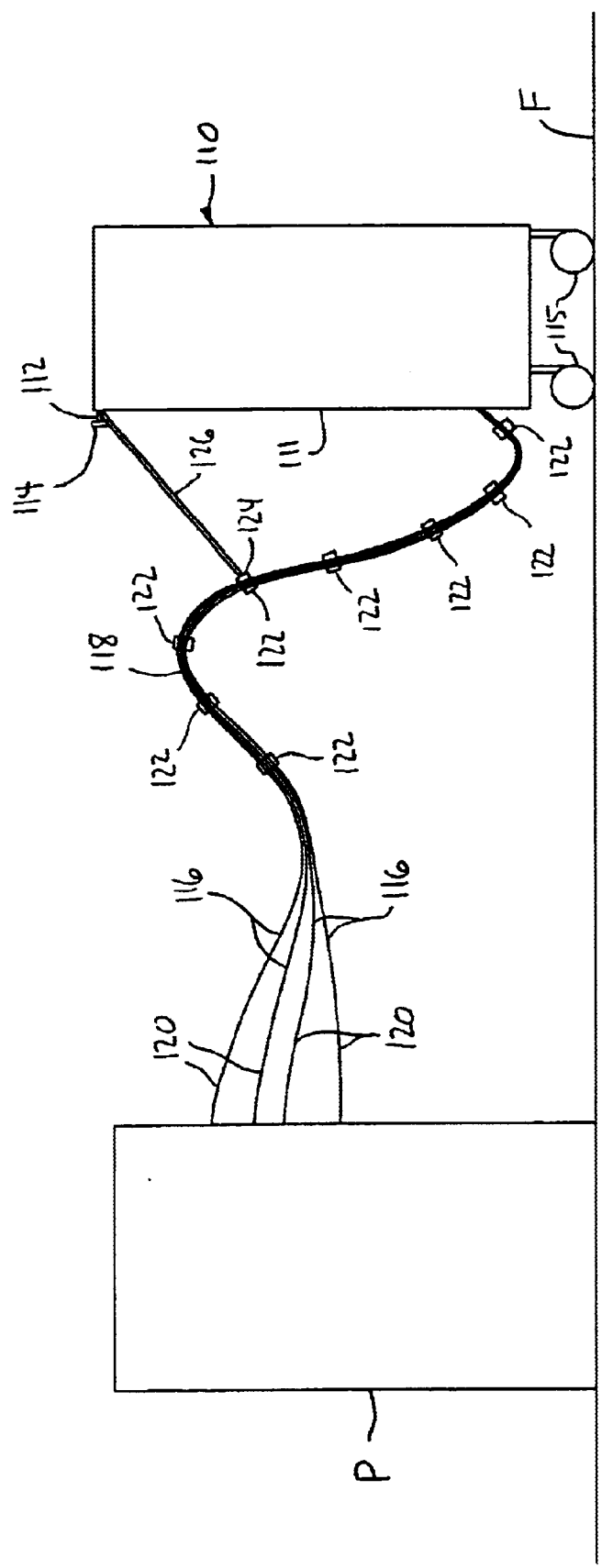
FIG. 2 illustrates the kidney dialysis machine shown in FIG. 1 located in a patient station and modified per the present invention.

FIG. 2 illustrates the kidney dialysis machine 110 modified per the present invention. The machine 110 is freestanding on the floor F of the work area of a conventional patient station P. A plurality of conventional flexible members 116 extend from the machine housing 111 and connect the machine with a number of station operating connections away from the machine. Four members 116 are shown, but the number and types of members 116 can vary among kidney dialysis machines.

The flexible members 116 are arranged to form a cable 118. The cable extends from the machine 110 a substantial portion of the overall length of the members 116. At the end of the cable the individual free ends 120 of the flexible members 116 separate from the cable bundle and extend to their respective station connections. A number of spaced apart cable ties 122 are wrapped around the flexible members to hold the cable together. The cable ties 122 preferably completely encircle the cable at their respective cable locations. The location, number and spacing of the ties can vary as needed. Each tie may not necessarily encircle all the members 116.

One cable tie 124 is attached to an end of an elongate coil spring 126. The other end of the spring 126 is mounted on the shaft 112 and held by knob 114. The coil spring is preferably a metal tension spring with coil loops on each end to form convenient attachment points. The coil spring holds the cable tie 124 above the floor and thereby lifts the cable 118 off the floor, preferably lifting the entire cable 118 above the wheels of the kidney dialysis machine.

The cable will not knot and will not catch in the wheels if the machine is relocated within the patient station. The spring 126 expands axially as necessary to permit the machine 110 to be moved away from the station connections and contracts to pick up cable slack if the machine is moved closer to the station connections. The length, stiffness and attachment points of the spring 126 can be adapted for use with different machines or station setups.

Other types of retaining members or springs could be used if desired. For example, the spring could be a torsion spring operatively connected to a take-up reel mounted on the machine 110. A flexible cord or line may be wound on the reel with the free end of the cord or line attached to the cable tie 124. The spring could also be made from an inherently elastic material, such as rubber.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A kidney dialysis machine for treating a dialysis patient at a patient station, the dialysis machine comprising:

a housing and a wheeled base supporting the housing on the floor of the patient station, the housing containing membrane means for dialysis;

a plurality of elongate flexible members extending from the housing to free ends of the members, each free end configured to connect to a corresponding connection of the patient station spaced away from the housing;

a retaining member attached to the plurality of flexible members to form a bundle of flexible members, the retaining member located along the flexible members intermediate of the housing and the free ends of the members; and a spring extending between the retaining member and the housing, the spring comprising one end operatively connected to the retaining member and another end operatively connected to the housing, the spring disposed to generate a spring force raising the retaining member off the floor whereby the bundle of flexible members does not contact the floor.

2. The kidney dialysis machine as recited in claim 1 wherein the retaining member comprises a cable tie wrapped around the plurality of flexible members.

3. The kidney dialysis machine as recited in claim 1 wherein the spring comprises a metal tension spring.

4. The kidney dialysis machine as recited in claim 1 comprising one or more additional retaining members attached to the flexible members, the additional retaining members spaced apart from each other and cooperatively defining a cable bundle of flexible members extending along a length of the flexible members.

5. The kidney dialysis machine of claim 1 wherein the machine is free standing.

6. The kidney dialysis machine of claim 5 comprising one or more additional retaining members attached to the flexible members, the additional retaining members spaced apart from each other along a length of the flexible members and cooperatively defining a cable bundle of flexible members extending along the length.

7. The kidney dialysis machine of claim 1 wherein the retaining member comprises a cable tie wrapped around the plurality of flexible members and the spring comprises a metal tension spring.

8. The kidney dialysis machine of claim 1 comprising a threaded shaft on the housing onto which the spring is mounted.

* * * * *